United States Patent [19]

Bruns et al.

[11] Patent Number: 5,765,759
[45] Date of Patent: Jun. 16, 1998

[54] REMOVABLE NOZZLE FOR A SANDBLASTER HANDPIECE

[75] Inventors: Craig R. Bruns; Thomas S. Blake; Mark S. Fernwood, all of Contra Costa, Calif.

[73] Assignee: Danville Engineering, San Ramon, Calif.

[21] Appl. No.: 562,528

[22] Filed: Nov. 27, 1995

[51] Int. Cl.$^6$ .................................................. A62C 5/00
[52] U.S. Cl. .......................... 239/398; 239/433; 239/600; 433/88
[58] Field of Search .................................. 239/398, 407, 239/427, 433, 600; 433/83, 87, 88; 51/427, 438

[56] References Cited

U.S. PATENT DOCUMENTS

| | | | |
|---|---|---|---|
| 2,641,087 | 6/1953 | Grerser | 51/12 |
| 2,744,361 | 5/1956 | Larson et al. | 51/11 |
| 3,164,153 | 1/1965 | Zorzi | 128/224 |
| 3,972,123 | 8/1976 | Black | 433/88 |
| 4,369,607 | 1/1983 | Bruggeman et al. | 51/427 |
| 4,522,597 | 6/1985 | Gallant | 433/216 |
| 4,676,749 | 6/1987 | Mabille | 433/88 |
| 4,776,794 | 10/1988 | Meller | 433/216 |
| 4,941,298 | 7/1990 | Funwood et al. | 433/88 |
| 5,082,185 | 1/1992 | Evans | 239/433 |
| 5,094,615 | 3/1992 | Bailey | 433/88 |
| 5,199,229 | 4/1993 | Herold et al. | 433/88 |
| 5,203,698 | 4/1993 | Blake et al. | 433/88 |
| 5,350,299 | 9/1994 | Gallant | 433/88 |
| 5,468,148 | 11/1995 | Ricks | 433/80 |

FOREIGN PATENT DOCUMENTS

| | | |
|---|---|---|
| 1027336 | 11/1950 | France. |
| 19173 | 11/1992 | WIPO. |

*Primary Examiner*—Andres Kashnikow
*Assistant Examiner*—Lisa Ann Douglas
*Attorney, Agent, or Firm*—Cooley Godward LLP

[57] ABSTRACT

A removable nozzle head for a minature sandblaster used for medical or industrial applications is disclosed comprising a nozzle, a handpiece nozzle adapter, a nozzle locking ring where the nozzle and nozzle handapiece adapter each have corresponding first and second bore in fluid communication to allow delivery of independent supplies of a gas and an abrasive laden stream to a mixing chamber in the nozzle for delivery through a orifice tube to a surface to be abraded, cleaned or modified.

22 Claims, 4 Drawing Sheets

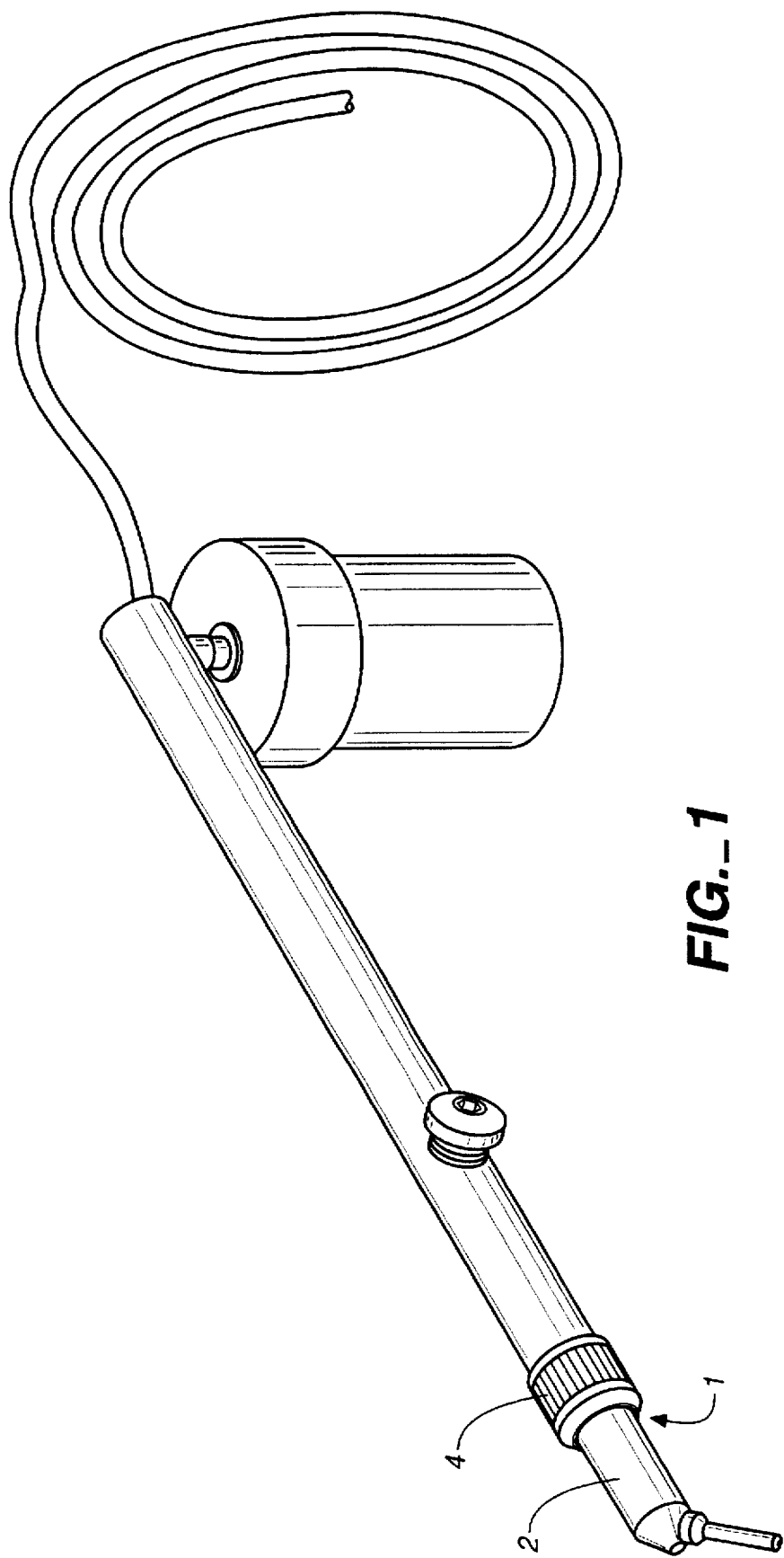
FIG._1

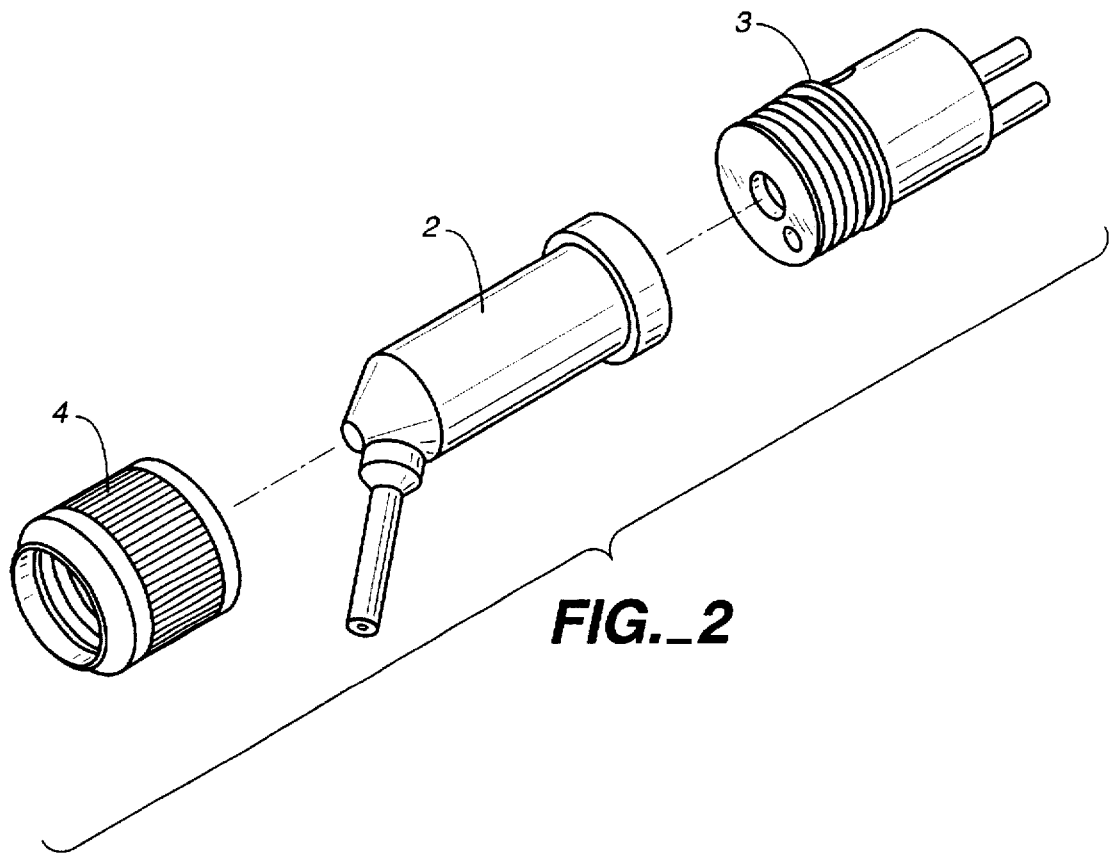
FIG._2
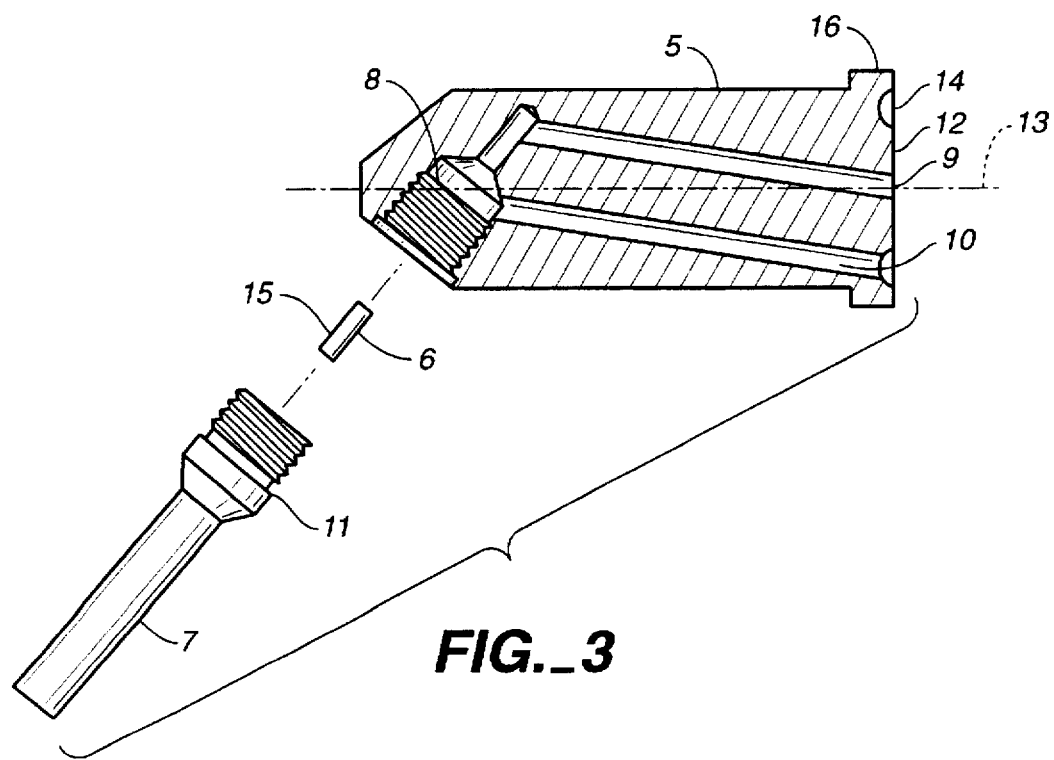
FIG._3

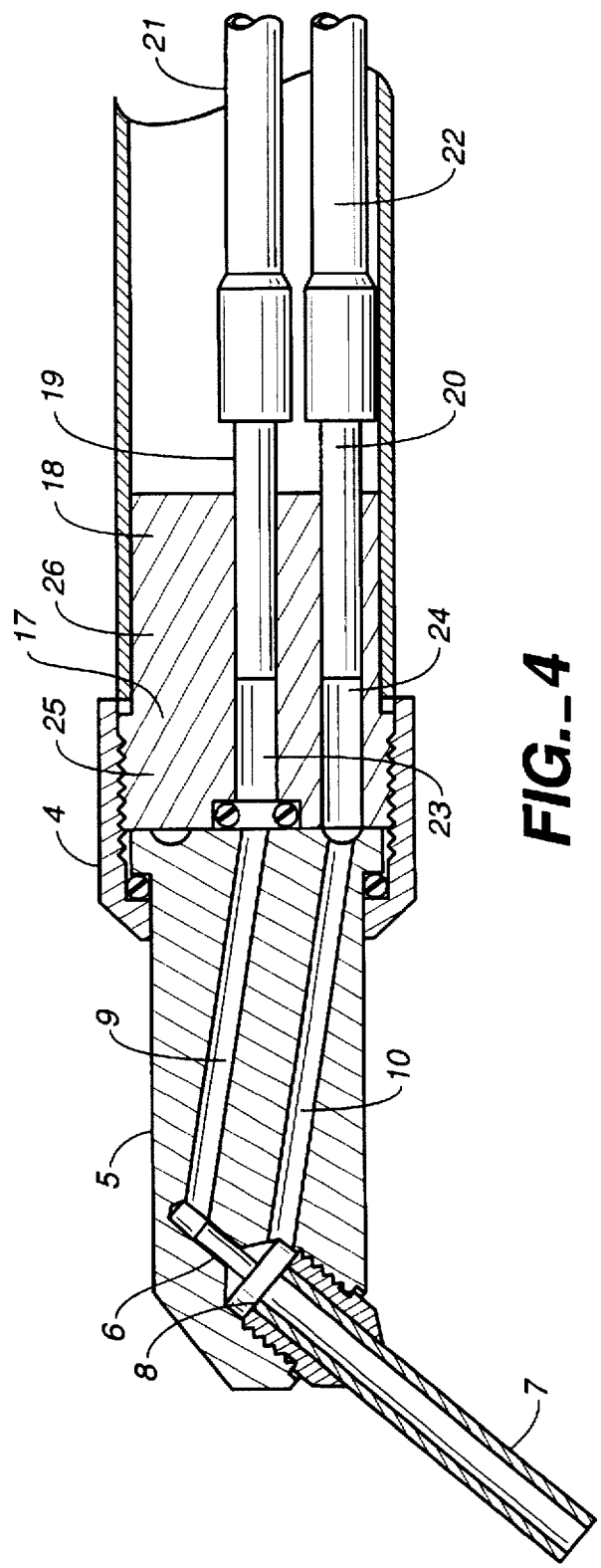
FIG._4

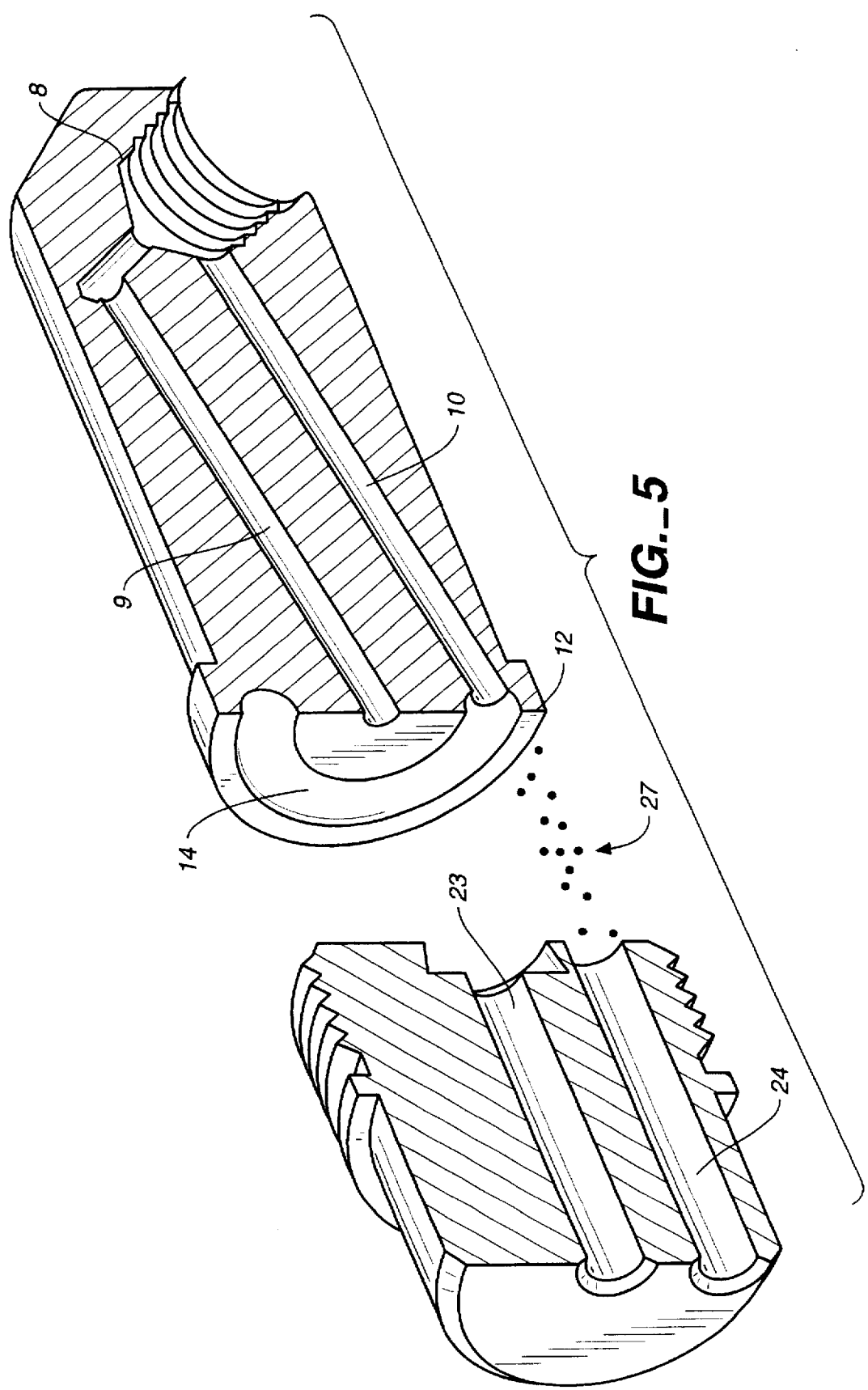
FIG._5

REMOVABLE NOZZLE FOR A SANDBLASTER HANDPIECE

CROSS REFERENCES TO RELATED APPLICATIONS

There are no related pending applications.

Background - Field of Invention

The present invention is directed to a nozzle head for the handpiece of a medical or industrial sandblaster apparatus. The sandblasting procedures encompassed range from cutting, cleaning, removing, modifying and prophylactic uses. In its primary field of use, dentistry, the device is useful in conjunction with a sandblasting apparatus to remove tooth structure for cavity preparation, remove existing composite fillings, roughen dental surfaces, whether tooth or restorative materials prior to adhesive bonding, to clean dental surfaces and a variety of other dental procedures known in the art. Industrial sandblasting applications are well known for which the described improved device is particularly well suited.

Background - Description of Prior Art

Precision sandblasters of various types are well known in the prior art. Designs for particular types of removable nozzle heads are also well known. These nozzles can be thought of as a simple conduit where only one stream is transmitted through the nozzle and where no additional abrasive or other materials are mixed within the nozzle. The nozzle type described herein allows for additional material to be mixed with the primary material supplied to the nozzle, or alternatively allows two materials to be concurrently transported through a nozzle from a remote supply.

For most sandblasting procedures, the ability to rotate the nozzle to better direct the abrasive laden stream greatly increases the utility and ease of use. Prior miniature sandblasters similar to that described in this application including one previously patented by applicants do not incorporate removable nozzle means despite the fact that they have nozzle rotation means incorporated. In one of applicants prior patented sandblasters, Fernwood, U.S. Pat. No. 4,941,298, the nozzle is capable of being rotated 180 degrees from the center line of the handpiece. Continued rotation however can cause air and abrasive lines inside the handle to become twisted and pinched resulting in inconsistent sandblasting action. Further as the nozzle is not designed for easy removal, material which clogs the nozzle may require disassembly of the entire sandblaster. Although sterilization is of little concern in industrial applications, when used as a medical device sterilization between patients is important and can not be conveniently and economically accomplished with prior art devices. Devices like our prior sandblaster, Fernwood, U.S. Pat. No. 4,941,298 generally require sterilization by liquid chemicals for exposure times up to ten hours. Other prior art devices such as a device by Deldent, Ltd. (not patented) can be heat sterilized in shorter time periods but still require that the entire device be sterilized Nov. 25, 1995 because the nozzle is not designed to be removed during normal use.

OBJECTS AND ADVANTAGES

The disclosed device shows a removable nozzle for a sandblaster with Accordingly, several objects and advantages of my invention are Objects and Advantages Description Still further objects and advantages will become apparent from a consideration of the ensuing description and accompanying drawings.

BRIEF DESCRIPTION OF THE DRAWINGS

FIG. 1 is a perspective view of the nozzle head shown installed on a micro sandblaster.

FIG. 2 is a perspective drawing of the nozzle head assembly.

FIG. 3 is a side view of the nozzle.

FIG. 4 is a crossectional view of the nozzle head.

FIG. 5 is a perspective view of the nozzle and nozzle adapter.

PREFERRED EMBODIMENT - DESCRIPTION

The improved nozzle head 1 comprising a nozzle, nozzle to handpiece adapter and a locking ring to hold the nozzle in direct contact with the nozzle adapter are illustrated installed on a microsandblaster in FIG. 1. FIG. 2 depicts a exploded view of the nozzle head. Shown in FIG. 2 is the nozzle 2, the nozzle adapter 3, the locking ring 4.

FIG. 3 depicts in greater detail the nozzle 2 which comprises generally the nozzle body 5, an acceleration jet 6, an exit orifice tube 7, a mixing chamber 8, and a first 9 and second 10 longitudinal bore for transmition of a gas and abrasive laden stream. Also shown in FIG. 3 is an exit orifice tube mount 11 which allows for easy removal in the event the exit tube becomes clogged, damaged or worn. The mount is an optional feature and could be eliminated by gluing or press fitting the exit orifice tube directly into the nozzle body. FIG. 3 also depicts a nozzle with an exit tube 7 angled downward at approximately a 60 degree angle. Various other angled tubes from zero degrees approaching to 180 degrees have been produced and are available depending upon the users applications. Now describing the nozzle body more specifically, FIG. 3 illustrates a first 9 and a second 10 longitudinal bore eminating from the rearward face 12 of the nozzle body also known as the nozzle adapter interface and terminating in the said mixing chamber 8. The first longitudinal bore 9 in the preferred embodiment acts as a conduit for a pressurized gas source passing in fluid connection through the gas acceleration orifice or jet and terminating in the mixing chamber. The first longitudinal bore eminates at the rearward end 12 of the nozzle body and is located at the central longitudinal axis 13 of the nozzle body. The second longitudinal bore 10 acts as a conduit for a stream of abrasive laden gas. The second bore eminates at the rearward face of the nozzle and is located radially from the central axis 13 of the nozzle and is in fluid communication with a centrally located annular groove 14 located in the rearward face of the nozzle. The second bore terminates in the mixing chamber and in the preferred embodiment has its central axis directed at the forward end 15 of the acceleration jet. At the rearward face of the nozzle, shown in FIG. 3 is a nozzle shoulder flange 16. The flange extends radially beyond the outer sides of the nozzle and provides a locking means to engage the nozzle locking ring and thereby secure the rearward face to the nozzle adapter.

Now turning to FIG. 4, the nozzle locking ring is shown installed. The nozzle locking ring slips over the exit orifice tube, over the nozzle body and engages the nozzle flange. In the preferred embodiment the nozzle locking ring has internal threads on the inner diameter which of course corresponds to the outer diameter threads of the forward end of the nozzle adapter. The nozzle locking ring is knurled on its outer diameter surface to allow for easy hand tightening.

FIG. 4 also depicts the nozzle adapter. The nozzle adapter comprises a nozzle adapter body, handpiece engagement means 18 and attachment means 19,20 for a first 21 and second 22 supply hose. In the preferred embodiment the nozzle adapter body is formed as a ring member, has first 23 and second 24 bores which when engaged with the nozzle provide for fluid communication between the first 9 and second 10 bores of the nozzle and the first 21 and second 22 supply hoses. The first and second bores corresponding to the first and second bore diameters in the nozzle body. Referring more specifically to FIG. 4, the nozzle adapter body has a forward end 25 and a rearward end 26. The first and second bores each have a pocket bore extending axially rearward. A first 19 and second 20 hollow plug is inserted and pressfit in each pocket bore. The first hollow plug serves as a slip-on means for a first supply line through which air is supplied. The second hollow plug serves as a slip-on means for a second supply line through which an abrasive laden gas stream passess.

Preferred Embodiment - Operation

Referring now to FIG. 5, the benefits of the described nozzle head are illustrated. For illustration purposes, although axially aligned the nozzle and nozzle adapter are not shown in face to face engagement and the locking ring is not depicted. During operation a gas passes through a first supply line through the first hollow plug and into the first 23 or center bore of the nozzle adapter and continues into the first 9 or center bore of the nozzle body eventually passing into the mixing chamber 8. Concurrently, a second supply line carrying a mixture of abrasive and a gas 27 passes through the second hollow plug through the second bore 24 of the nozzle adapter, and enters the corresponding second bore 10 of the nozzle body eventually passing into the mixing chamber where the two streams are mixed and then propelled through the exit orifice tube (not shown). When the nozzle body is rotated around its central longitudinal, the second bore of the nozzle adapter and the second bore of the nozzle body will no longer be axially aligned, they however remain in fluid communication through the annular groove 14 in the rearward face 12 of the nozzle body. FIG. 5 illustrates that when the second bores' 24, 10 are not axially aligned the abrasive exists the nozzle adapter, passes around and through the annular groove 14 and into the second bore of the nozzle body. The fact that the annular groove keeps both second bores' in fluid connection independent of the nozzle body rotation overcomes a significant disadvantage of existing designs.

In the preferred embodiment the nozzle body is fabricated of aluminum and the nozzle adapter of stainless steel. Altough the exact materials are somewhat insignificant, applicant feel that the more wear resistant material should be used for the nozzle adapter as compared to the nozzle body. With this material preference, the easily replaced nozzle body will wear out before the nozzle adapter which is generally affixed to the handpiece. The annular groove could be located in either the nozzle adapter or the nozzle body. For machining ease, in the preferred embodiment the annular groove is located in the softer nozzle body material.

The described removable nozzle head may be effectively used when the first and second supply line pressures are approximately equal. When the second supply line is at atmospheric pressure, the first supply line must be sufficiently pressurized such that the gas passing through the acceleration jet causes a venturi effect thereby creating a vaccuum on the second bores' and second supply line resulting in an urging of abrasive to flow into the mixing chamber. Generally air pressures in the range of 25 to 100 psi or more produce a sufficient venturi effect to urge abrasive particles into the mixing chamber. To avoid pressure or vaccuum losses from occuring between the second bores' at the interface between the nozzle body and the nozzle adapter, the faces' must be highly polished and aligned with high precision. Alternatively flexible sealing o-rings may be located at the interface between the nozzle flange and the locking ring internal diamter flange. For simplicity and economical reasons o-rings are used in the preferred embodiment.

In order to easily heat sterilize the nozzle, all components of the nozzle are fabricated from materials with operating temperatures of at least 400 degrees fahrenheit.

Applicants also note that the supply line could be changed without a problem if the supply streams are at roughly equal pressures. Additionally, the mixing chamber could be eliminated under an alternative embodiment where the intended desire is to deliver two independent streams beyond the nozzle exit orifice. For this alternative embodiment the nozzle head described herein can be easily modified to accomplish this intended objective by placing the acceleration jet in airtight fluid communication with the exit orifice tube such that the stream delivered through the first bore can not mix with second supply stream until both streams exit the nozzle. Under this configuration, the second stream delivered to the formerly labeled mixing chamber can be transported from the nozzle by second orifice exit tube, or by other means known to those skilled in the art such as longitudinal grooves along the sides of the first exit orifice tube.

It accordingly should be understood that various modifications and variations will no doubt occur to those skilled in the art to which this invention pertains. All such modifications and variations which basically rely on the teachings through which this disclosure has advanced the are therefore properly considered within the scope of this invention as defined by the appended claims.

Conclusions, Ramifications, and Scope

Accordingly, it can be seen that disclosed nozzle head provides a novel removable head which can be easily rotated, removed for repair, replacement or sterilization and can accomodate nozzles with varying angled orifice tubes.

Although the description above contains many specificities, these should not be construed as limiting the scope of the invention but as merely providing illustrations of some of the presently preferred embodiments of this invention. Various other embodiments and ramifications are possible within it's scope. Thus the scope of the invention should be determined by the appended claims and their legal equivalents, rather than by the examples given.

What is claimed is:

1. A nozzle head having a forward end and a rearward end, which nozzle head comprises a first longitudinal bore, a second longitudinal bore located radially from the first longitudinal bore, each first and second bore leading to a mixing chamber within the forward end of the nozzle head, an exit orifice tube leading out of the mixing chamber, and a face at the rearward end of the nozzle head, said face having an annular groove in fluid communication with said second longitudinal bore and having a centrally located opening for the first longitudinal bore not in fluid communication with the annular groove.

2. The nozzle head of claim 1 wherein the exit orifice tube is not removable from the nozzle head.

3. The nozzle head of claim 1 wherein an acceleration jet is located within the mixing chamber.

4. The nozzle head of claim 1 wherein the exit orifice tube is removable from the nozzle head.

5. The nozzle head of claim 4 wherein the exit orifice tube screws into the nozzle head.

6. The nozzle head of claim 1 wherein a shoulder flange extends radially beyond the outer side of the rearward end of the nozzle head.

7. The nozzle head of claim 6 in combination with a locking ring that engages the shoulder flange for attachment to a nozzle adapter.

8. A sandblaster apparatus that comprises (A) a nozzle head, (B) a nozzle head adapter, and (C) a locking ring to attach the nozzle head to the nozzle head adapter, wherein (A) the nozzle head has a forward end and a rearward end and further comprises
- a first longitudinal bore,
- a second longitudinal bore located radially from the first longitudinal bore,
- each first and second bore leading to a mixing chamber within the forward end of the nozzle head,
- an exit orifice tube leading out of the mixing chamber,
- a face at the rearward end of the nozzle head, said face having an annular groove in fluid communication with said second longitudinal bore and having a centrally located opening for the first longitudinal bore not in fluid communication with the annular groove, and a shoulder flange that extends radially beyond the outer side of the rearward end of the nozzle head;

(B) the nozzle head adapter comprises a body having a forward end and rearward and a first fluid-carrying bore in fluid communication with said first longitudinal bore in the nozzle head and a second fluid-carrying bore in fluid communication with said annular grove and second longitudinal bore in the nozzle head; and (C) the locking ring engages the flange on the nozzle head to attach the nozzle head to the adapter.

9. The apparatus of claim 8 wherein the first longitudinal bore in the nozzle head and the first fluid carrying bore in the adapter are in fluid communication with a source of gas and the second longitudinal bore in the nozzle head and the second fluid-carrying bore in the adapter are in fluid communication with a source of a pressurized gas carrying abrasive particles, so that a stream of gas and a stream of gas carrying abrasive particles mix in the mixing chamber and exit through the exit tube.

10. The apparatus of claim 8 wherein an acceleration jet is located within the mixing chamber in the nozzle head.

11. The apparatus of claim 10 wherein the exit orifice tube is removable from the nozzle head.

12. The apparatus of claim 11 wherein the exit orifice tube screws into the nozzle head.

13. The apparatus of claim 12 wherein the exit orifice tube is not removable from the nozzle head.

14. The apparatus of claim 8 wherein the locking ring removably fits over the exit orifice tube and nozzle head to engage the shoulder flange to retain the rearward end of the nozzle head attached to the forward end of the nozzle head adapter.

15. The apparatus of claim 8 wherein the locking ring permanently attaches the nozzle head to the nozzle head adapter.

16. A method for abrading a surface using a nozzle head for a sandblaster handpiece in combination with a sandblaster handpiece, which method comprises positioning the sandblaster handpiece nozzle head over a surface to be abraded at an appropriate angle and distance while passing a gas through a first supply line and an abrasive material through a second supply line into a mixing chamber and into a nozzle head wherein said nozzle head comprises
- a first longitudinal bore,
- a second longitudinal bore located radially from the first longitudinal bore,
- each first and second bore leading to the mixing chamber within the forward end of the nozzle head,
- an exit orifice tube leading out of the mixing chamber, and
- a face at the rearward end of the nozzle head, said face having an annular groove in fluid communication with said second longitudinal bore and having a centrally located opening for the first longitudinal bore not in fluid communication with the annular groove.

17. The method of claim 16 wherein the exit orifice tube is not removable from the nozzle head.

18. The method of claim 16 wherein an acceleration jet is located within the mixing chamber.

19. The method of claim 16 wherein the exit orifice tube is removable from the nozzle head.

20. The method of claim 19 wherein the exit orifice tube screws into the nozzle head.

21. The method of claim 16 wherein a shoulder flange extends radially beyond the outer side of the rearward end of the nozzle head.

22. The method of claim 21 wherein the shoulder flange is combined with a locking ring that engages the shoulder flange for attachment to a nozzle adapter of the sandblaster.

* * * * *

(12) REEXAMINATION CERTIFICATE (4482nd)
United States Patent
Bruns et al.

(10) Number: US 5,765,759 C1
(45) Certificate Issued: Nov. 6, 2001

(54) REMOVABLE NOZZLE FOR A SANDBLASTER HANDPIECE

(75) Inventors: Craig R. Bruns; Thomas S. Blake; Mark S. Fernwood, all of Contra Costa, CA (US)

(73) Assignee: Danville Engineering, San Ramon, CA (US)

Reexamination Request:
No. 90/005,803, Aug. 29, 2000

Reexamination Certificate for:
Patent No.: 5,765,759
Issued: Jun. 16, 1998
Appl. No.: 08/562,528
Filed: Nov. 27, 1995

(51) Int. Cl.[7] ................................ B05B 7/04; A61C 3/02
(52) U.S. Cl. .......................... 239/398; 239/433; 239/600; 433/88
(58) Field of Search .................................. 239/398, 407, 239/427, 433, 600; 433/83, 87, 88; 51/427, 438

(56) References Cited

U.S. PATENT DOCUMENTS

| | | | |
|---|---|---|---|
| 3,421,702 | 1/1969 | O'Brien | 239/418 |
| 3,905,554 | 9/1975 | Bell | 239/424 |
| 4,648,840 | 3/1987 | Conger, Sr. | 433/125 |

FOREIGN PATENT DOCUMENTS

| | | | |
|---|---|---|---|
| 32 42 306 C2 | 5/1984 | (DE) | B05B/7/02 |
| 31 01 632 C2 | 8/1982 | (DE) | B05B/7/04 |
| 38 41 069 A1 | 3/1991 | (DE) | B05B/9/04 |
| 0 225 193 B1 | 6/1987 | (EP) | B05B/7/04 |
| 91/03640 | 3/1991 | (WO) | B05B/1/00 |

*Primary Examiner*—Lesley D. Morris

(57) ABSTRACT

A removable nozzle head for a minature sandblaster used for medical or industrial applications is disclosed comprising a nozzle, a handpiece nozzle adapter, a nozzle locking ring where the nozzle and nozzle handapiece adapter each have corresponding first and second bore in fluid communication to allow delivery of independent supplies of a gas and an abrasive laden stream to a mixing chamber in the nozzle for delivery through a orifice tube to a surface to be abraded, cleaned or modified.

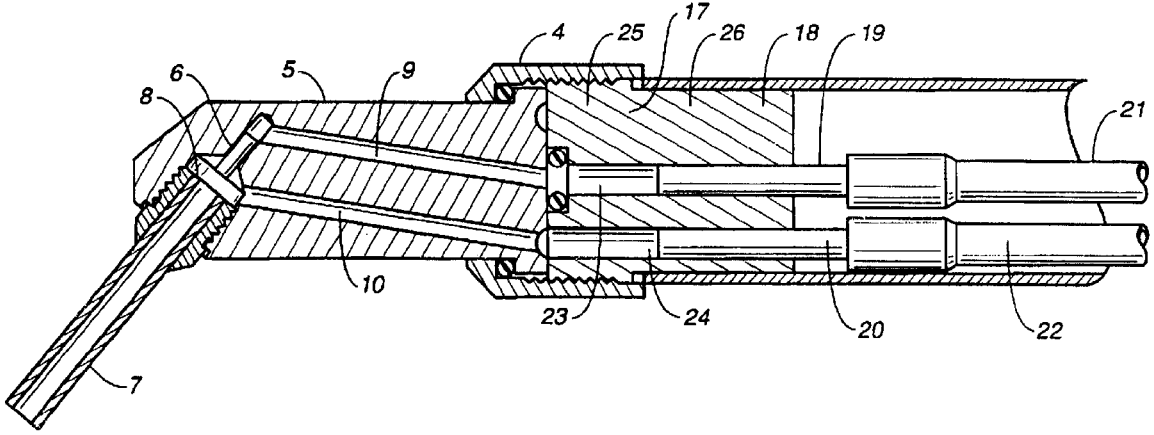

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 8–22 is confirmed.

Claim 6 is cancelled.

Claims 1 and 7 are determined to be patentable as amended.

Claims 2–5, dependent on an amended claim, are determined to be patentable.

New claims 23–30 are added and determined to be patentable.

1. A nozzle head having a forward end and a rearward end, which nozzle head comprises
   a first longitudinal bore,
   a second longitundinal bore located radially from the first longitudinal bore,
   each first and second bore leading to a mixing chamber within the forward end of the nozzle head,
   an exit orifice tube leading out of the mixing chamber, [and]
   a face at the rearward end of the nozzle head, said face having an annular groove in fluid communication with said second longitudinal bore and having a centrally located opening for the first longitudinal bore not in fluid communication with the annular groove[.], *and*
   *a shoulder flange extending radially beyond the outer side of the rearward end of the nozzle head.*

7. The nozzle head of claim [6] *1* in combination with a locking ring that engages the shoulder flange for attachment to a nozzle adapter.

*23. A nozzle head for combination with a handpiece for use in medical or industrial sandblasting operations, the nozzle head having a forward end and a rearward end and comprising*
   *a first longitudinal bore;*
   *a second longitudinal bore located radially from the first longitudinal bore;*
   *each first and second bore leading to a mixing chamber suitable for mixing abrasive particles with a gas stream, which chamber is within the forward end of the nozzle head;*
   *an exit orifice tube leading out of the mixing chamber;*
   *a face at the rearward end of the nozzle head, said face having an annular groove in fluid communication with said second longitudinal bore and having a centrally located opening for the first longitudinal bore not in fluid communication with the annular groove; and*
   *means for removably securing the nozzle head to the handpiece so that the nozzle head may be rotated about a central longitudinal axis perpendicular to said face.*

*24. The nozzle head of claim 23, wherein the exit orifice tube is not removable from the nozzle head.*

*25. The nozzle head of claim 23, wherein an acceleration jet is located within the mixing chamber.*

*26. The nozzle head of claim 23, wherein the exit orifice tube is removable from the nozzle head.*

*27. The nozzle head of claim 26, wherein the exit orifice tube screws into the nozzle head.*

*28. The nozzle head of claim 23 wherein the means for removably securing the nozzle head is a shoulder flange extending radially beyond the outer side of the rearward end of the nozzle head.*

*29. The nozzle head of claim 28, in combination with a locking ring that engages the shoulder flange for attachment to a handpiece.*

*30. The nozzle head of claim 23, for combination with a handpiece for use in dental sandblasting operations.*

* * * * *